(12) United States Patent
Weitschies et al.

(10) Patent No.: US 7,033,841 B1
(45) Date of Patent: Apr. 25, 2006

(54) PROCESS AND COMPOUNDS FOR USE IN DETECTING ANALYTES BY MEASUREMENT OF RESIDUAL MAGNETISM, AND THE USE OF THE SAID COMPOUNDS

(75) Inventors: Werner Weitschies, Berlin (DE); Roman Kötitz, Berlin (DE); Lutz Trahms, Berlin (DE); Thomas Bunte, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 08/894,767

(22) PCT Filed: Feb. 29, 1996

(86) PCT No.: PCT/EP96/00823

§ 371 (c)(1),
(2), (4) Date: Feb. 23, 1998

(87) PCT Pub. No.: WO96/27133

PCT Pub. Date: Sep. 6, 1996

(30) Foreign Application Priority Data

Mar. 1, 1995 (DE) .......................................... 195 08 772

(51) Int. Cl.
*G01N 33/533* (2006.01)

(52) U.S. Cl. ................ 436/526; 436/501; 436/149; 436/173; 436/800; 435/7.1

(58) Field of Classification Search ................ 436/526, 436/501, 148, 173, 806; 435/7.1
See application file for complete search history.

(56) References Cited

U.S. PATENT DOCUMENTS

| | | | | | |
|---|---|---|---|---|---|
| 4,724,390 | A | * | 2/1988 | Rauscher et al. ........... 324/344 |
| 4,824,587 | A | * | 4/1989 | Kwon et al. .............. 252/62.55 |
| 4,849,210 | A | * | 7/1989 | Widder ........................... 424/9 |
| 4,913,883 | A | * | 4/1990 | Imai et al. ................ 422/82.01 |
| 5,164,297 | A | * | 11/1992 | Josephson et al. .......... 435/7.25 |
| 5,427,767 | A | * | 6/1995 | Kresse et al. .............. 424/9.32 |
| 5,464,696 | A | * | 11/1995 | Tournier et al. ............. 428/403 |
| 5,492,814 | A | * | 2/1996 | Weissleder ................. 435/7.25 |
| 5,597,531 | A | * | 1/1997 | Liberti et al. .................. 423/57 |
| 5,628,983 | A | * | 5/1997 | Klaveness et al. ........ 424/9.364 |
| 6,027,946 | A | * | 2/2000 | Weischies et al. ........... 436/526 |

FOREIGN PATENT DOCUMENTS

| | | |
|---|---|---|
| DE | 3013827 C2 | 10/1980 |
| DE | 19514104 A1 | 11/1996 |
| DE | 19535729 A1 | 3/1997 |
| EP | 0123426 A2 | 10/1984 |
| EP | 0309345 A1 | 3/1989 |
| EP | 0487418 A1 | 5/1992 |
| EP | 0679373 A2 | 11/1995 |
| EP | 0747069 A2 | 12/1996 |
| EP | 0782864 A1 | 7/1997 |
| WO | WO 87/01040 A1 | 2/1987 |
| WO | WO 87/03608 A1 | 6/1987 |
| WO | WO 96/18498 A1 | 6/1996 |

OTHER PUBLICATIONS

JP 07–088173 Patent Abstract.
JP 08–224295 Patent Abstract.
USP 4,508,916 English Abstract (equilvalent to DE 3013827).
WO 96/32143 English Abstract (equivalent to De 19514104).

* cited by examiner

*Primary Examiner*—Christopher L. Chin
*Assistant Examiner*—Pensee Do
(74) *Attorney, Agent, or Firm*—Millen White Zelano & Branigan, P.C.

(57) ABSTRACT

The invention relates to a process for quantitative detection of analytes in liquid and solid phases with the aid of binding remanence measurement, compounds that are suitable for this purpose, and their use in analytic chemistry.

36 Claims, 2 Drawing Sheets

Figure 1:
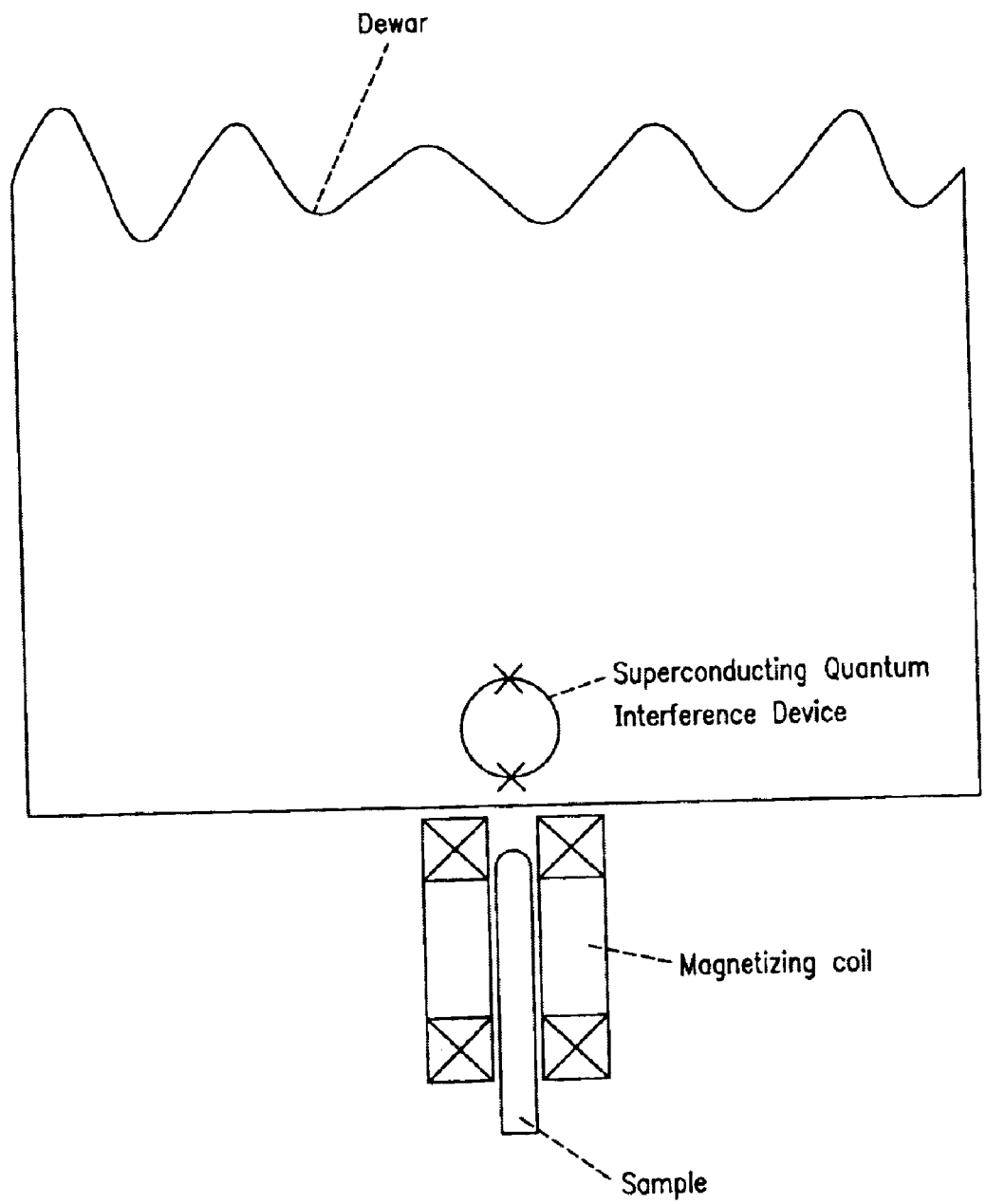

PROCESS AND COMPOUNDS FOR USE IN DETECTING ANALYTES BY MEASUREMENT OF RESIDUAL MAGNETISM, AND THE USE OF THE SAID COMPOUNDS

The invention relates to the object that is characterized in the claims, i.e., a process for qualitative and/or quantitative detection of analytes in liquid and solid phases using remanence measurement, compounds that are suitable for this purpose, and their use in analytic chemistry.

It is known that quantitative immunoassays, as well as other binding assays (e.g., receptor binding assays) make it possible to determine a very large number of substances that can also be of biological relevance in samples of varying compositions. Generally, however, only one parameter per sample in an assay is determined in this way. An existing survey of the various processes is: T. Chard [An Introduction to Radioimmunoassay and Related Techniques: Laboratory Techniques in Biochemistry and Molecular Biology, 4th ed., Elsevier Science Publishers, Amsterdam (1990)]. The basis of all binding assays is the high detection sensitivity of compounds that are labeled with isotopes or by some other means in combination with the high specificity of ligand-receptor reactions.

The known assay processes have the following drawbacks, however:

The processes for simultaneous determination of various analytes within the same sample are based on the binding of varying radio-, fluorescence- or enzymological-labeled probes to the analytes. In this case, the unbound or bound activity of the probe for quantitative determination of the analyte is generally measured after subsequent separation and washing. In this case, the amounts of usable different probe labels are very limited. Thus, for example, in the case of different radioisotopes as probe labeling, so-called overlapping phenomena occur, which lead to a rapid loss of the quantitative accuracy of individual signals. Combining various enzymes as probe labels causes comparable problems, whereby implementation is additionally hampered here by the necessary search for reaction conditions that allow the simultaneous determination of enzyme reactions in a system.

The sensitivity of the process is limited by, for example, non-specific interactions between matrix and probe, or else by limited labeling capability of the probe (low specific activity).

The successful implementation of the process often requires that the sample material obtained be worked up (e.g., production of serum or plasma from whole blood, extraction of samples with organic solvents, concentration of the analyte using chromatographic processes, etc.).

For successful implementation of the processes, separation and washing steps, which ensure the separation of bound and unbound receptors or ligands, are essential.

For implementation of radioimmunoassays, the use of radiating nuclides, which are costly and complicated to handle, is necessary.

In practice, the storage of the used markers often causes problems since they either are not stable (as in the case of radioimmunoassays) and therefore always have to be made fresh or else react to environmental influences in a sensitive manner.

The object of this invention was therefore to find a novel process and substances that are superior to the above-mentioned prior art.

This object is achieved by this invention.

It has been found that the qualitative and/or quantitative detection of analytes in liquid and/or solid phases is possible if stable or quasi-stable ferromagnetic or ferrimagnetic substances are used as magnetic labeling that is to be identified in immunoassays or binding assays and the remanent magnetization of the sample is determined as a measurement variable.

Below, processes that overcome the drawbacks of the known processes are first described.

The processes according to the invention are based on the use of colloidal ferromagnetic or ferrimagnetic substances, also referred to below as magnetic labeling, that are combined with substances that are to be identified—also referred to below as analytes—or structure-specific substances. Such combinations of magnetic labelings with analytes or structure-specific substances are also referred to below as magnetic markers. The use of the term colloidal substances is intended to describe both the range of sizes of the particles or substances in the range of sizes of colloids, i.e., the range of 1 nm up to about 1000 nm, and their use as a dispersed phase in a suitable dispersion medium, which is aqueous in most cases. Colloidal substances, which are also referred to below as particles, can also be present in dried form or frozen for the purpose of improved shelf life and transportability; during the execution of measurements, however, they are generally present in the liquid-phase dispersed state.

An important principle of the invention is that the time-dependence of the magnetization of ferromagnetic or ferrimagnetic colloidal substances after an external magnetizing field is shut off depends in a very sensitive manner on the material and form (anisotropy constants of the particle material used), volume and temperature of the particles used. This is caused by rotation of the internal magnetizing vector within the particles. This mechanism is referred to as Neelian relaxation. If the magnetization of the particles relaxes within the measurement time, the superparamagnetism is referred to as intrinsic. Particles whose Neelian relaxation times are considerably longer than the observation period are referred to as remanent particles or as stable particles. Particles whose Neelian relaxation times are on the order of the observation period are referred to as quasi-stable particles.

Another essential principle of the invention is that the magnetization of a totality of freely-movable stable or quasi-stable ferromagnetic or ferrimagnetic colloidal particles relaxes within the measurement time owing to a second mechanism after an external magnetizing field is shut off. In this case, rotation of the entire colloidal particle occurs within the surrounding liquid, whereby the time constant depends on the hydrodynamic diameter of the particles including the shell, the viscosity of the carrier liquid, and temperature. These parameters are determined mainly by the environment of the particles. The mechanism is referred to as Brownian relaxation or extrinsic superparamagnetism.

The process according to the invention for qualitative and/or quantitative detection of analytes in liquid and solid phases is carried out by i) structure-specific substances first being labeled with ferrimagnetic or ferromagnetic substances, and then ii) these magnetically labeled structure-specific substances being used in a sample that is to be measured, iii) with the sample to be measured being magnetized with the aid of a magnetic field of suitable intensity that is applied from the outside and, iv) after the external field is shut off, the remanence of the magnetization of the colloidal particles (magnetic labeling) being measured with the aid of magnetic field sensors, whereby the remanence that occurs due to specific binding and its extent are used for analysis.

In the processes of the prior art, the discrimination that was possible only in exceptional cases between bound and unbound markers is made possible in the process according to the invention by the use of the fading remanence (i.e., extrinsic superparamagnetism) of the unbound, magnetic markers in the liquid phase. The totality of the bound magnetic markers, however, show a measurable remanence that depends on the particle material. In measuring the remanence of the sample to be determined, only the portion of bound magnetic markers is thus detected. The process is therefore also referred to below as measuring binding remanence or binding remanence measurement and is based on the quantitative detection of bound structure-specific markers.

In other words, the determination of the analyte can also be done without expensive separation and washing steps since only the stable or quasi-stable ferromagnetic or ferrimagnetic substances that are specifically bound to the analytes (which are combined with structure-specific substances for the purpose of imparting a specificity) cause remanence, while the magnetization of excess, unbound stable or quasi-stable ferromagnetic or ferrimagnetic substances that are simultaneously present in the sample (which are also combined with structure-specific substances) fades even before the beginning of the measurement by extrinsic superparamagnetism.

In another embodiment of the invention, the process is modified in such a way that instead of the structure-specific substances, the analytes themselves are combined with the stable or quasi-stable ferromagnetic or ferrimagnetic substances, as is often used analogously in, e.g., the execution of competitive radioimmunoassays. The structure-specific substance then has to be additionally added to the samples.

The process can also be implemented as a multianalyte assay, however, which makes possible direct simultaneous determination of several different analytes in liquids or solids. To this end, it is necessary first to label the analytes with different ferromagnetic or ferrimagnetic colloidal substances with sufficiently discrete coercive field intensities. During the binding of the magnetic markers, a magnetizing field (primary magnetizing field) is applied, which causes all magnetic markers that are contained in the sample to be oriented along their simple axis.

Then, the remanence of the sample is determined. In further steps, the sample is demagnetized with external counter-fields (running counter to the primary magnetizing field), which are matched in their intensity to the coercive field intensities of the magnetic labelings. As a result, it is possible always to re-orient specifically only those labelings whose coercive field intensities are lower than the applied magnetizing field. The remanence of the sample is again determined in each case between the individual steps of the demagnetization.

The portion of different bound magnetic markers can thus be quantified based on the measured remanences of the sample in each individual demagnetization step.

This process makes it possible to determine several analytes per sample simultaneously.

The process according to the invention, as well as variants of the process, can be used in fertility, histocompatibility, allergology, infectiology, hygiene, genetics, virology, bacteriology, toxicology, pathology, environmental analysis, and medical diagnosis.

The detection of binding remanence is carried out with known measurement arrangements that are suitable for this purpose, such as, for example, Superconducting Quantum Interference Devices (SQUIDs), whereby first magnetization is done with the aid of a suitable magnetic field, and then the measurement of the remanence of the magnetized structure-specific substance or signals that are dependent thereon is done using sensitive magnetic field sensors after the field is shut off.

During measurement, the sample can advantageously be moved. Especially advantageous is modulation of the signal by vibration or rotation of the sample. This ensures transformation of the dc-measuring signal to a higher frequency range.

For measurement—in addition to the above-mentioned SQUIDs—induction coils that are hooked up as gradiometers, fluxgate-magnetometers, giant magnetoresistance sensors, or magnetoresistive converters can also be used.

When sensors that can measure dc fields (e.g., SQUIDs, fluxgate-magnetometers, giant magnetoresistance sensors, or magnetoresistive converters) are used, measurement of remanence after preceding magnetization of the sample is also possible, without the latter being moved.

A suitable measurement arrangement is depicted by way of example in FIG. 1. Such an arrangement was also used in the examples below.

Another aspect of the invention relates to compounds for measuring binding remanence. Suitable compounds consist of colloidal suspensions, ferrimagnetic or ferromagnetic substances, and structure-specific substances or analytes.

Within the framework of this invention, structure-specific substances are defined as all substances that bind specifically to the desired structure, such as, e.g., antibodies, antibody fragments, biotin, or substances that bind specifically to biotin such as avidin or streptavidin, agonists that bind specifically to receptors, such as cytokines, lymphokines, endothelins or their antagonists, specific peptides and proteins, receptors, enzymes, enzyme substrates, nucleotides, ribonucleic acids, deoxyribonucleic acids, carbohydrates, lipoproteins, etc. Among them, substances are preferred whose binding constant is in the range of $10^5$–$10^{15}$ (mol/l)$^{-1}$, and especially substances whose binding constant is in the range of $10^7$–$10^{15}$ (mol/l)$^{-1}$.

As ferromagnetic or ferrimagnetic colloidal substances, all ferromagnetic and ferrimagnetic substances can be used whose intrinsic Neelian relaxation time is greater than or equal to the measuring time and which thus are stable or quasi-stable.

Especially suitable are all ferromagnetic and ferrimagnetic substances whose relaxation time is longer than $10^{-4}$ second at 20° C. Especially suitable are all ferromagnetic and ferrimagnetic substances whose relaxation time is longer than 1 second.

The ferromagnetic and ferrimagnetic substances can advantageously be stabilized with a shell made of oligomeric or polymeric carbohydrates, proteins, peptides, nucleotides, surfactants, synthetic polymers, and/or lipids.

The particle sizes of the ferromagnetic and ferrimagnetic substances are advantageously between 1 nm and 1000 nm. Especially preferred are particle sizes of between 2 nm and 500 nm. (The values with respect to particles sizes relate to hydrodynamic diameter.)

As ferromagnetic or ferrimagnetic substances, especially stable or quasi-stable colloidal particles that consist of iron oxides ($Fe_3O_4$, $\gamma$—$Fe_2O_3$), barium ferrite, strontium ferrite, pure iron, chromium dioxide, nickel, cobalt as well as iron oxides with manganese, copper, nickel or cobalt additives (as described in, e.g., DE 30 27 012 and DE 41 16 093), are suitable.

The production of the compounds that can be used according to the invention that consist of stable or quasi-stable ferromagnetic or ferrimagnetic substances, which are connected to structure-specific substances or analytes, is carried out by means of processes that are familiar in the area of immunochemistry, peptide chemistry, and protein chemistry. In this case, the structure-specific substance or the analyte is linked via covalent bonds to the substances that form the stabilizing shell of the ferromagnetic or ferrimagnetic substances. As stabilizing shells, e.g., carbohydrates, peptides, nucleotides, proteins, lipids, surfactants, or polymers are suitable. Especially suitable linkage methods are, e.g., activation and coupling using carbodiimides [Jakoby and Wilchek, eds., (1974) Methods Enzymol 34], the formation of Schiff bases after periodates act on compounds that contain carbohydrates (Wichek and Bayer, eds., Methods Enzym 184:177), which optionally are then again reduced for further stabilization, coupling using glutaric dialdehyde [Heitzmann and Richards, Proc. Natl. Acad. Sci. USA, 71 (1974) 3537], the crosslinking of bromoacetylated particles with thiolylated substances (Angerer et al., Cell 9 (1976) 81], and reductive alkylation [Bayer et al., J. Histochem. Cytochem. 24 (1976) 933].

Ferromagnetic or ferrimagnetic colloidal particles can also be produced with a stabilizing shell made of the structure-specific substance or the analyte itself, by the particles being brought after production either directly into a solution of the structure-specific substance or the analyte, optionally in the presence of other adjuvants, such as, e.g., proteins, carbohydrates as well as natural, synthetic or partially synthetic surfactants, or being produced directly in the presence of structure-specific substances or analytes.

For the purpose of performing multianalyte assays, mixtures of compounds that consist of several different magnetic markers can also be used, whereby the different magnetic markers consist of combinations of different structure-specific substances or analytes that are to be identified with different ferromagnetic or ferrimagnetic substances. The principle of this use of combinations of different magnetic markers according to the invention is that ferromagnetic or ferrimagnetic substances with varying coercive field intensities ($H_C$) are used as magnetic labeling for the respective structure-specific substances or analytes that are to be identified, whereby the parameters of coercive field intensity ($H_C$) and remanent magnetization ($M_R$) for the different magnetic labelings can be determined separately in advance in a known way and thus are known.

The structure-specific substances that are labeled with the ferromagnetic or ferrimagnetic colloidal substances can also be present in dried form (e.g., as lyophilizates), optionally in combination with other adjuvants which facilitate drying or increase the stability of the dried product (e.g., as lyophilizates). The production of the agents that are ready-for-use from such lyophilizates is then carried out by resuspension in a suitable suspension medium immediately before use.

Another aspect of the invention thus relates to ferromagnetic or ferrimagnetic colloidal substances that contain agents for binding remanence measurement in a suitable suspension medium.

As suspension media, all liquids are suitable in which the colloidal particles can move freely. If the measurements are carried out without separation or washing steps, the viscosity of the suspension medium that is used has to be matched to the Neelian relaxation time of the ferromagnetic and ferrimagnetic substances and the measuring time since the suspension medium basically determines the time constant of the Brownian relaxation. Otherwise, e.g., when using particles with a short relaxation time (e.g., 0.01 second) in highly viscous suspension media (e.g., 80% glycerol) and at short measurement times (e.g., 0.0001 second after the external field is shut off), Brownian relaxation (extrinsic superparamagnetism) can be slowed to such an extent that a distinction can no longer be made between bound and unbound structure-specific markers. It is generally advantageous to use suspension media of a viscosity of less than 100 mPas.

As suspension media, water, aqueous solutions of surface-active adjuvants, such as, e.g., surfactants or oligomeric or polymeric carbohydrates and proteins, as well as mixtures of water with alcohols such as, e.g., glycerol and polyethylene glycol, are suitable, whereby water that is suitable for injection purposes is preferred. In addition, the suspension media can contain adjuvants that change the osmotic pressure, such as, e.g., common salt. In addition, buffer substances that determine pH, such as, e.g., phosphates, may be contained.

Another object of the invention is the use of compounds in the process according to the invention for measuring binding remanence.

Due to the binding identification based on physical mechanisms, non-specific measurement signals (matrix phenomena) can be largely ruled out. The specificity of the process thus depends only on the "true" specificity of the structure-specific substance (cross reactivity of antibodies, non-specific binding of ligands).

Due to the high sensitivity of the process according to the invention, it is easy to remain under the detection limits of binding assays that are otherwise commonly encountered.

In contrast to known methods (JP-235774 and WO 91/15243), in the process according to the invention, it is not static magnetization that is measured in the presence of an external magnetizing field but rather, in the absence of a magnetizing field, the binding remanence or signals dependent thereon. Only in this way are data on the binding state of the markers made available.

In addition, this keeps the measuring signal from being influenced by diamagnetic or paramagnetic components or contaminants; this helps to further increase measuring sensitivity.

The processes for binding remanence measurement according to the invention can additionally be used to identify in vivo the retention sites of ferromagnetic or ferrimagnetic substances. In this case, it is of special advantage that ferromagnetic or ferrimagnetic substances can be used to determine binding remanence and thus the especially critical use of radioactive isotopes in humans is avoided, whereby the sensitivity of the process according to the invention reaches that of commonly used nuclear-medicine processes of gamma scintigraphy or positron emission tomography. Moreover, prior separation of unbound markers that circulate in the blood is not necessary since the latter (in contrast to radiodiagnostic methods) does not cause any "interfering signal," and thus the detection of specifically bound markers is not affected.

According to the invention, a suspension of stable or quasi-stable ferromagnetic or ferrimagnetic substances is administered to the patient. Local application, peroral administration, and all forms of parenteral administration are suitable as administration methods. Especially suitable are intravascular forms of administration.

Colloidal substances are dispersed in the organism, whereby the distribution pattern in the body is influenced by the method of administration, as well as by various other pharmacokinetic parameters. The site-resolved determination of binding remanence can be used at different times after administration of stable or quasi-stable ferromagnetic or ferrimagnetic substances to determine pathologic states in the body, which are characterized both by unusual concentrations or by the failure of concentrations to occur.

For visualization of pathological structures in the human body, the use of stable or quasi-stable ferromagnetic or ferrimagnetic substances (magnetic markers) combined with structure-specific substances can be especially advantageous. Here, the specific binding of the magnetic markers to the pathological structure results in a specific signal, which can be determined in vivo according to the invention with the processes of binding remanence that are described for carrying out binding assays.

As an example of an application of stable or quasi-stable ferromagnetic or ferrimagnetic substances in combination with the process of binding remanence measurement according to the invention, the detection of tumors in the body using tumor-specific magnetic markers can be mentioned. Tumor-specific markers can be, e.g., combinations of stable or quasi-stable ferromagnetic or ferrimagnetic substances with tumor-specific substances, such as, e.g., antibodies, antibody fragments, peptides, receptors, proteins, nucleic acids, oligonucleotides, and monomeric, oligomeric, or polymeric carbohydrates.

Other examples of possible applications are the visualization of clots, arteriosclerotic plaques, inflammatory reactions, and rheumatic or rheumatoid alterations, whereby in each case it is advantageous to use as magnetic markers combinations of stable or quasi-stable ferromagnetic or ferrimagnetic substances according to the invention with specific substances for the respective pathologic structure.

The in-vivo measurement of the spatial distribution of stable or quasi-stable magnetic markers that are administered to a human is carried out according to the invention according to two variants:

1. Generating as homogeneous a magnetic field as possible in the advantageous body regions, shutting off the field, and measuring the spatial distribution of the binding remanence using a SQUID-multichannel sensor, as is used for, e.g., biomagnetic tests [cf. D. Drung, IEEE Trans. Appl. Supercond., 5 (1995) 2112–2117]. This sensor should enclose the measuring object as completely as possible. To produce sufficient measuring information, re-measurement with sequential rastering of the measuring object is advantageous.
2. Sequentially generating a spatially limited local field, shutting off the field, and measuring the spatial binding remanence using a single-channel sensor. The use of a multichannel sensor is also possible.

With both methods, both magnetization of the measurement object and measurement of the resulting magnetic field in all three spatial directions is to be preferred to ensure that maximum information is collected.

The evaluation of the measuring data can be done using a suitable approximation process. Thus, e.g., the model of the magnetic dipole, multipole, or multi-dipole can be taken as the point of departure. The special parameters of the model, particularly the locations of the dipoles or multipoles, are then found using the approximation process, which minimizes the deviations between measurement data and model parameters. The spatial distribution of the magnetized particles can be determined from these parameters in a way known in the art.

An analogous approach is known and has proven itself in analyzing the magnetic fields of bioelectric currents.

For the measurement of binding remanence in vivo, basically the same substances—or agents that are prepared from them—as are also used in in vitro tests are suitable.

Especially suitable for in-vivo application are magnetic labelings that are biodegradable and compatible. This is especially true of magnetic labelings that consist of iron oxides or combinations of iron oxides with manganese or cobalt. Magnetic particles to which structure-specific substances can be linked according to the known processes are used in, e.g., nuclear spin tomography and are described in, i.a., WO 92/12735, WO 92/22586 as well as EP 0 186 616. Another aspect of the invention thus relates to the use of magnetic labelings in an in-vivo process for measuring binding remanence.

In connection with the in-vivo application of binding remanence measurement, structure-specific substances are defined especially as all substances that bind specifically to structures of the human body that are to be identified. Especially suitable are antibodies, antibody fragments, agonists that bind specifically to receptors or their antagonists, specific peptides and proteins, receptors, enzymes, enzyme substrates, nucleotides, ribonucleic acids, deoxyribonucleic acids, carbohydrates, or lipoproteins. Of the agonists that bind to receptors, especially cytokines, lymphokines, or endothelins are suitable.

Well suited are all structure-specific substances that have a binding constant in the range of $10^5$–$10^{15}$ $(mol/l)^{-1}$. Especially suitable are all structure-specific substances that have a binding constant in the range of $10^7$–$10^{15}$ $(mol/l)^{-1}$.

The following examples are used to provide a more detailed explanation of the object of the invention, without intending that it be limited to these examples.

Example 1

100 µg of a monoclonal antibody to collagen III, referred to below as anticollagen III, is dissolved in 500 µl of a 0.1 M sodium bicarbonate solution. 1 ml of dextran-coated magnetite suspension (Meito Sangyo) with 1 mol of Fe/l and a particle size of about 40 nm (hydrodynamic diameter) is buffered with 0.1 M sodium bicarbonate on a Sephadex column (Pharmacia PD 10). 0.5 ml of 10 mmol sodium periodate solution is added to the suspension. The solution is allowed to stand in the dark for 2 hours. Then, it is eluted on a PD 10 with 0.1 M sodium bicarbonate solution. The anticollagen III solution is added to the suspension. The mixture is allowed to stand in the dark for 3 hours at 4° C. Then, 5 mg of $NaBH_4$ is added as a solid and briefly swirled. The mixture is allowed to stand in the dark for 8 hours at 4° C. Then, the magnetite-labeled anticollagen III (referred to below as mag-anticollagen III) is eluted via a PD 10 column with phosphate-buffered common salt solution (PBS, pH 7.4).

A solution of 5 µg of collagen III in 200 µl of buffer [phosphate-buffered common salt solution (PBS)] is incubated in a polystyrene sampling vessel. (The sampling vessel serves in this case as a solid phase, to which a portion of the collagen is attached.) The liquid phase is then discarded. The sampling vessel is flushed three times with phosphate-buffered common salt solution, containing 0.1% Tween$^{(R)}$ 20 (referred to as PBST below), to wash out unattached collagen. In the sampling vessel, 5 µl of mag-anticollagen III, dissolved in 200 µl of PBST, is then added. It is incubated for 1 hour at room temperature. Then, the sample is magnetized in a magnetically shielded chamber in a field with an intensity of 2 mT 4 cm below the squid detector (see FIG. 1). After the magnetic field is shut off, the sample is measured. To this end, the sample is removed from the magnetizing coil during measurement. The remanence is produced from the difference of the determined magnetic flux densities—after the magnetic field is shut off—before and after the sample is removed from the measuring field. In the case of this example, a remanence was found.

Example 2

A solution of 5 µg of collagen V in 200 µl of PBS buffer of pH 7.4 is incubated in a sampling vessel made of polystyrene. Then, the liquid phase is discarded. The sampling vessel is flushed three times with PBST washing buffer of pH 7.4. 5 µl of mag-anticollagen III, produced according to Example 1, in 200 µl of PBST is added to the sample. It is incubated for 1 hour at room temperature. Then, the sample is magnetized in a magnetically shielded chamber in a field with an intensity of 2 mT 4 cm below the SQUID detector (see FIG. 1). After the magnetizing field is shut off, the sample is measured. To this end, the sample is removed from the magnetizing coils during measurement. In the sample that contains collagen V, no remanence can be detected.

Exampl 3

From 10 ml of a 1.9 mg/ml collagen III solution in PBS (pH 7.4), 5 ml each of the following dilutions is produced:

1,000 ng/ml, 100 ng/ml, 10 ng/ml

In each case 1 ml apiece is pipetted from each dilution into a polystyrene tube (2.5 ml capacity). The three sample tubes are inhibited for 1 hour at 37° C. Then, the contents of the tubes are discarded. The tubes are washed three times with 1 ml of PBST each.

Figure 2:
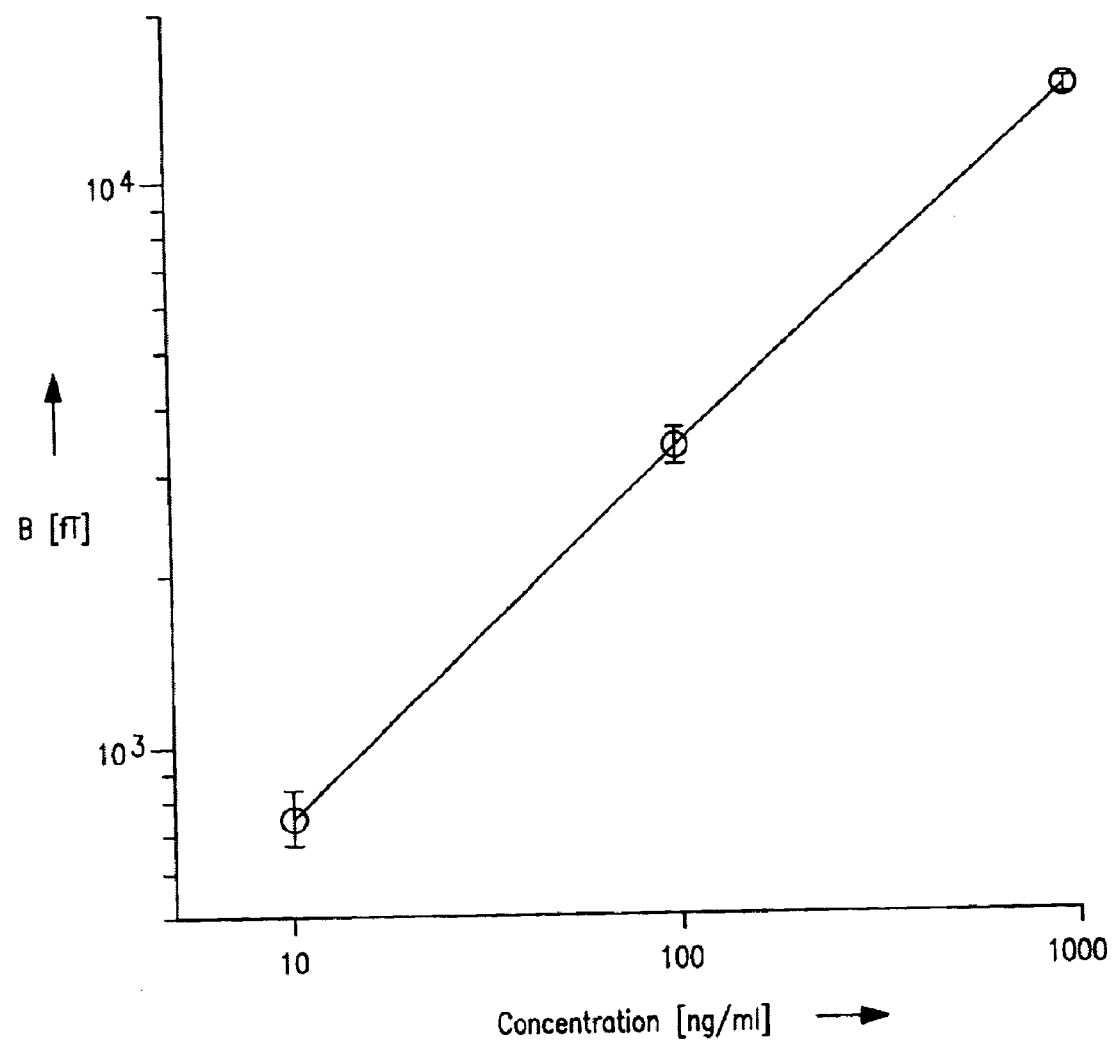

1 ml of a 1:100 dilution of the magnetite-labeled antibody, produced according to Example 1, is added to each tube. The tubes are allowed to stand for 1 hour at room temperature. Then, the samples are magnetized (2 mT) with the measuring arrangement outlined in FIG. 1 and, after the magnetizing field is shut off, the samples are measured. To this end, the samples are removed from the magnetizing coils during measurement. The evaluation of the measured signals is a measure of binding remanence and yields the relationship shown in FIG. 2.

What is claimed is:

1. A process for qualitative and/or quantitative detection of analytes in a liquid and/or solid phase homogeneous immunoassay, comprising determining remanence magnetization in said homogeneous immunoassay of a stable or quasi-stable ferromagnetic or ferrimagnetic substance bound to said analyte, wherein said homogeneous immunoassay has been connected with said ferromagnetic substance, whereby said substance binds to the analyte, and the presence of such magnetization is indicative of the presence or amount of the analyte.

2. The process according to claim 1, wherein the sample is moved during the measurement and a sample signal is modulated.

3. The process according to claim 1, wherein induction coils that are hooked up as gradiometers, fluxgate-magnetometers, giant magnetoresistance sensors, or magnetoresistive converters are used as magnetic field sensors to determine remanent magnetization.

4. The process according to claim 1, wherein SQUIDs are used as magnetic field sensors to determine remanent magnetization.

5. The process according to claim 1, wherein simultaneous determination of several different analytes in a sample of liquids or solid substances is carried out by sequential magnetization of a sample to be measured.

6. The process according to claim 5, wherein the simultaneous quantitative determination of analytes, different ferromagnetic or ferrimagnetic substances with discrete coercive field intensities are used.

7. The process according to claim 5, wherein several ferromagnetic or ferrimagnetic substances with various coercive field intensities are used.

8. The process according to claim 1, wherein the ferromagnetic and ferrimagnetic substances used have intrinsic Neelian relaxation times greater than the measuring time.

9. The process according to claim 8, wherein the ferromagnetic and ferrimagnetic substances that are used have Neelian relaxation times longer than $10^{-4}$ seconds at 20° C.

10. The process according to claim 8, wherein the ferromagnetic and ferrimagnetic substances that are used have Neelian relaxation times longer than 1 second at 20° C.

11. The process according to claim 1, wherein the ferromagnetic and ferrimagnetic substances have a particle size of 1 to 1000 nm.

12. The process according to claim 1, wherein the ferromagnetic and ferrimagnetic substances have a particle size in the range of 2 to 500 nm.

13. The process according to claim 1, wherein the ferromagnetic and ferrimagnetic substances are stabilized with a shell of oligomeric or polymeric carbohydrates, proteins, peptides, nucleotides, surfactants, synthetic polymers, and/or lipids.

14. The process according to claim 1, wherein the ferromagnetic or ferrimagnetic substances are stable or quasi-stable colloidal particles that are made of iron oxides, barium ferrite, strontium ferrite, pure iron, chromium dioxide, nickel and cobalt, or iron oxides with manganese, copper, nickel or cobalt additives.

15. In a fertility, histocompatibility, allergology, infectiology, hygiene, genetics, virology, bacteriology, toxicology, pathology, environmental analysis, or medical diagnosis process comprising detecting an analytes, the improvement wherein the detecting is performed according to claim 1.

16. The process according to claim 1, wherein ferromagnetic and ferrimagnetic substances are introduced into the human body or are applied on the human body, and the remanence of the magnetization of the ferromagnetic or ferrimagnetic substances is determined after a magnetizing field is shut off.

17. The process according to claim 16, wherein Superconducting Quantum Interference Devices (SQUIDs), induction coils, fluxgate-magnetometers, giant magnetoresistance sensors, or magnetoresistive converters are used as magnetic field sensors.

18. The process according to claim 16, wherein the Neelian relaxation time of the ferromagnetic or ferrimagnetic substances is longer than $10^{-4}$ second at 37° C.

19. The process according to claim 18, wherein the ferrimagnetic or ferrimagnetic substances are iron oxides or iron oxides with manganese, copper, nickel, or cobalt additives.

20. The process according to claim 16, wherein the Neelian relaxation time for the ferromagnetic or ferrimagnetic substances is longer than 1 second at 37° C.

21. The process according to claim 1, wherein the ferromagnetic or ferrimagnetic substance is magnetic-labeled anticollagen III and SQUID(s) are used to determine remanent magnetization.

22. A process according to claim 1, wherein the ferromagnetic or ferrimagnetic substances are used to label structure specific substances, which are added to the analyte.

23. The process according to claim 22, wherein the structure-specific substances are antibodies, antibody fragments, biotin, substances that bind specifically to biotin, agonists that bind specifically to receptors of their antagonists, peptides, proteins, receptors, enzyme substrates, nucleotides, ribonucleic acids, deoxyribonucleic acids, carbohydrates or lipoproteins.

24. A process according to claim 1, wherein the analyte is labeled with structure specific substances, and the ferromagnetic or ferrimagnetic substances are added thereto.

25. A process according to claim 24, wherein the structure-specific substances are antibodies, antibody fragments, biotin, substances that bind specifically to biotin, agonists that bind specifically to receptors of their antagonists, peptides, proteins, receptors, enzyme substrates, nucleotides, ribonucleic acids, deoxyribonucleic acids, carbohydrates, or lipoproteins.

26. A process for qualitative and/or quantitative detection of analytes in homogeneous immunoassays comprising measuring remanence magnetization of magnetic markers in a sample, bound to said analytes, wherein said homogeneous immunoassay has been contacted with said ferromagnetic substance, whereby said substance binds to the analyte, and at the time of measurement the magnetization of unbound magnetic markers that are present in the sample in their totality fades owing to extrinsic superparamagnetism, and the presence of remanence magnetization is indicative of the presence or amount of said analytes.

27. A process for qualitative and/or quantitative detection of analytes in a liquid or solid phase homogeneous immunoassay, comprising
   (i) labeling first structure-specific substances, with ferrimagnetic or ferromagnetic substances to indicate the presence or amount of said analyte.
   (ii) adding said magnetic labeled structure-specific substances to a sample that is to be measured.
   (iii) magnetizing the sample to be measured with the aid of a magnetic field or suitable intensity that is applied from outside and,
   (iv) measuring the remanence of the magnetization of bound structure-specific substances with the aid of magnetic field sensors after the external field is shut off, without removing unbound structure-specific substances.

28. The process according to claim 27, wherein the structure-specific substances have a binding constant in the range of $10^5$–$10^{15}$ $(mol/l)^{-1}$.

29. The process according to claim 27, wherein the structure-specific substances have a binding constant in the range of $10^7$–$10^{15}$ $(mol/l)^-$.

30. The process according to claim 27, wherein the structure-specific substances are cytokines, lymphokines, endothelins or their antagonists.

31. The process according to claim 27, wherein ferromagnetic or ferrimagnetic substances are introduced into an organism or applied on the organism, by a process comprising
   (i) labeling structure-specific substances with ferromagnetic or ferrimagnetic substances,
   (ii) adding said magnetic labeled structure-specific substances to a living organism or applied to an organism,
   (iii) magnetizing a volume of the organism with the aid of a magnetic field that is applied from the outside and,
   (iv) measuring remanence of the magnetic markers with the aid of magnetic field sensors after the external field is shut off.

32. The process according to claim 31, wherein antibodies, antibody fragments, agonists that bind specifically to receptors or their antagonists, peptides, proteins, receptors, enzymes, enzyme substrates, nucleotides, ribonucleic acids, deoxyribonucleic acids, carbohydrates, or lipoproteins are used to structure-specific substances.

33. The process according to claim 32, wherein the agonists or antagonists that bind specifically to receptors are cytokines, lymphokines, endothelins or their antagonists.

34. The process according to claim 32, wherein the structure-specific substances have a binding constant in the range of $10^5$–$10^{15}$ $(mol/l)^{-1}$.

35. The process according to claim 32, wherein the structure-specific substances have a binding constant in the range of $10^7$–$10^{15}$ $(mol/l)^{-1}$.

36. The process according to claim 31, wherein a mixture of different ferromagnetic and ferrimagnetic substances with structure-specific substances is used.

* * * * *